(12) United States Patent
Buzzard et al.

(10) Patent No.: US 7,381,216 B2
(45) Date of Patent: *Jun. 3, 2008

(54) METHOD FOR LOCKING HANDLE DEPLOYMENT MECHANISM WITH MEDICAL DEVICE

(75) Inventors: Jon Buzzard, Miramar, FL (US); Frederick Feller, III, Margate, FL (US)

(73) Assignee: Cordi Corporation, Miami Lakes, FL (US)

( * ) Notice: Subject to any disclaimer, the term of this patent is extended or adjusted under 35 U.S.C. 154(b) by 765 days.

This patent is subject to a terminal disclaimer.

(21) Appl. No.: 10/820,968

(22) Filed: Apr. 8, 2004

(65) Prior Publication Data

US 2004/0193180 A1  Sep. 30, 2004

Related U.S. Application Data (60) Division of application No. 10/175,113, filed on Jun. 19, 2002, now Pat. No. 6,866,669, which is a continuation-in-part of application No. 09/975,873, filed on Oct. 12, 2001, now Pat. No. 6,939,352.

(51) Int. Cl.
*A61F 2/06* (2006.01)
(52) U.S. Cl. .................................... 623/1.11; 606/108
(58) Field of Classification Search .............. 606/108, 606/191, 194, 195, 198, 205, 207; 623/1.11
See application file for complete search history.

(56) References Cited

U.S. PATENT DOCUMENTS

| | | | |
|---|---|---|---|
| 4,665,918 A | 5/1987 | Garza et al. | |
| 4,990,151 A | 2/1991 | Wallstén | |
| 5,026,377 A | 6/1991 | Burton et al. | |
| 5,290,310 A | 3/1994 | Makower et al. | |
| 5,312,351 A | 5/1994 | Gerrone et al. | |
| 5,391,172 A | 2/1995 | Williams et al. | |
| 5,433,723 A | 7/1995 | Lindenberg et al. | |

(Continued)

FOREIGN PATENT DOCUMENTS

EP        0 873 733 A1    11/1998

(Continued)

OTHER PUBLICATIONS

European Search Report EP 02 25 7071 dated Dec. 8, 2003 with Annex to the European Search Report.

*Primary Examiner*—Michael Hayes
*Assistant Examiner*—Victor Nguyen
(74) *Attorney, Agent, or Firm*—Michael Montgomery (57) ABSTRACT

Methods for delivering at least one medical device to a desired location for treatment, and then selectively deploy it in position, include an improved handle. One of the possible features of the handle may be to selectively hold the delivery system components at any desired configuration during deployment and positioning of the medical device. Another possible feature of the handle may be more than one mode of operation, in which the deployment of the medical device can selectively proceed at more than one speed. Yet another possible feature of the handle may be a locking mechanism that resists inadvertent or accidental movement or retraction of the stent delivery system components during packaging, sterilization, shipping, storage, handling and preparation of the stent delivery system.

8 Claims, 10 Drawing Sheets

U.S. PATENT DOCUMENTS

| | | |
|---|---|---|
| 5,591,172 A | 1/1997 | Bachmann et al. |
| 5,601,568 A | 2/1997 | Chevillon et al. |
| 5,704,914 A | 1/1998 | Stocking et al. |
| 5,707,376 A | 1/1998 | Kavteladze et al. |
| 5,749,921 A | 5/1998 | Lenkar et al. |
| 5,759,186 A | 6/1998 | Bachmann et al. |
| 5,776,142 A | 7/1998 | Gunderson |
| 5,782,855 A | 7/1998 | Lau et al. |
| 5,868,755 A | 2/1999 | Kanner et al. |
| 5,891,154 A | 4/1999 | Loeffler |
| 5,906,619 A | 5/1999 | Olson et al. |
| 5,944,727 A | 8/1999 | Ahari et al. |
| 5,968,052 A | 10/1999 | Sullivan, III et al. |
| 6,019,778 A | 2/2000 | Wilson et al. |
| 6,143,021 A | 11/2000 | Staehle |
| 6,146,415 A | 11/2000 | Fitz |
| 6,190,360 B1 | 2/2001 | Iancea et al. |
| 6,203,550 B1 | 3/2001 | Olson |
| 6,402,760 B1 | 6/2002 | Fedida |
| 6,517,569 B2 | 2/2003 | Mikus et al. |
| 6,613,014 B1 | 9/2003 | Chi |
| 6,866,669 B2 * | 3/2005 | Buzzard et al. ............. 606/108 |
| 6,939,352 B2 * | 9/2005 | Buzzard et al. ............. 606/108 |
| 2001/0051822 A1 | 12/2001 | Stach et al. |
| 2002/0004683 A1 | 1/2002 | Gittings et al. |

FOREIGN PATENT DOCUMENTS

| | | |
|---|---|---|
| EP | 0 876 804 A1 | 11/1998 |
| FR | 2 797 761 A1 | 3/2001 |
| WO | WO 98/11846 A1 | 3/1998 |
| WO | WO 00/18330 | 4/2000 |
| WO | WO 02/087470 A1 | 11/2002 |

* cited by examiner

METHOD FOR LOCKING HANDLE DEPLOYMENT MECHANISM WITH MEDICAL DEVICE

REFERENCE TO RELATED APPLICATION

This patent application is a divisional patent application of U.S. patent application Ser. No. 10/175,113 filed on Jun. 19, 2002 now U.S. Pat. No. 6,866,669, which is a continuation-in-part of U.S. patent application Ser. No. 09/975,873 filed on Oct. 12, 2001 now U.S. Pat. No. 6,939,352.

BACKGROUND AND SUMMARY OF THE INVENTION

1. Technical Background

The present invention relates generally to medical devices, and more particularly to a medical device delivery system with an improved locking handle having a compound mechanism.

2. Discussion

The present invention involves medical devices, and also the delivery systems used to convey them to a desired location for treatment, and then deploy them in position. Many such medical devices are resiliently compressed to a smaller initial size for containment, protection, storage and eventual delivery from inside a catheter system. Upon deployment, the medical devices may resiliently expand to a larger deployed size.

Figure 10:
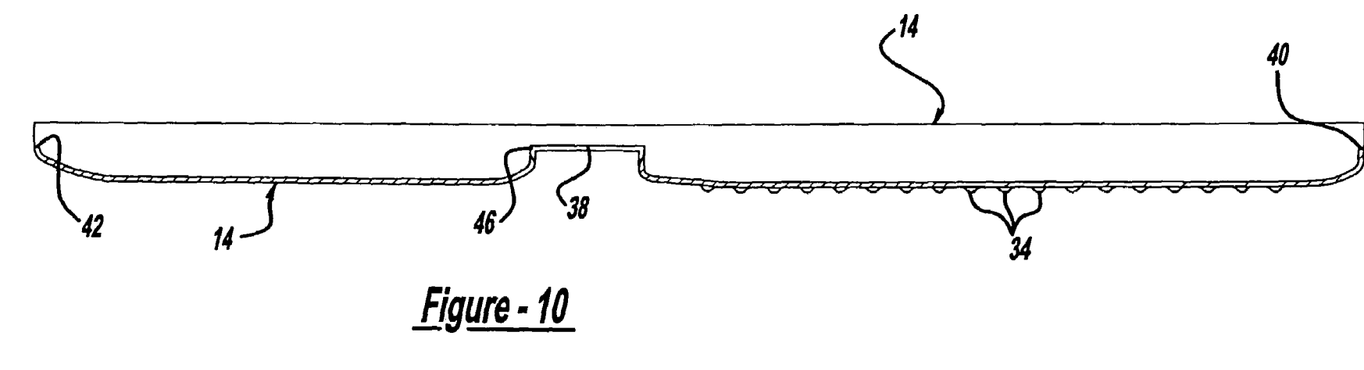

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al. Mar. 22, 1988.

In operation, these known medical device delivery systems are generally advanced within a body of a patient along a desired vascular path or other body passageway, until the medical device within the catheter system is located at a desired site for treatment. While watching the relative positions of the medical device and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a medical device as the outer sheath is retracted. This gradual expansion presents an opportunity for a possible reverse "watermelon-seed" phenomenon to occur. This reverse watermelon-seed effect may cause the resilient medical device to tend to push the outer sheath back in a proximal direction with a force that tends to change as the sheath is progressively retracted.

As a result, the physician may need to accurately hold the two proximal hubs in a specific relative position, holding them against this expansion force, while attempting to very accurately position the medical device up until contact with the anatomy. One of the possibilities that may affect the positioning of the deployed medical device is that the inner shaft should preferably be held stationary in the desired position. If the physician's hand that holds the inner shaft hub does inadvertently move during deployment, it is possible that the medical device may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the medical device may be adjusted up until the point at which a portion of the expanding portion of the medical device touches the sidewalls of the body passage, so that the position of the medical device should preferably be carefully adjusted until immediately before a portion of the medical device touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated medical device.

Accordingly, although physicians may be capable of operating such known systems with great skill, it is desirable to provide an improved catheter delivery system capable of facilitating easier and more accurate deployment and positioning of resiliently expansive medical device.

In addition, it is desirable to provide an advanced catheter-based deployment method having two modes of operation. In the first mode of operation, the delivery mechanism preferably provides a precisely adjustable link between the inner and outer catheter shaft members, such that the relative position of the outer sheath with respect to the inner catheter shaft member can be precisely and selectively adjusted. Yet at any selected position, the delivery mechanism should preferably maintain this selected relative position of the inner and outer catheter shaft members, while resisting any force that may be present tending to move the inner or the outer catheter shaft members with respect to the other. In a second mode of operation, the delivery mechanism should preferably enable the physician to rapidly withdraw the outer tubular sheath with respect to the inner catheter shaft member preferably in a proximal direction with a single easy motion.

It is also desirable to provide a handle for operating a stent delivery system that includes a locking mechanism. Such a locking mechanism preferably resists inadvertent or accidental movement or retraction of the stent delivery system components during packaging, sterilization, shipping, storage, handling and preparation. The lock preferably is spring-loaded, or otherwise easily released.

In addition, the handle mechanism may also provide for activation and retraction of the sheath only, while resisting an attempt to re-advance the sheath and re-cover the medical device.

Another embodiment of the present invention involves providing a single actuator for both or all of the multiple modes of operating the handle and delivery system.

Additional embodiments of the present invention relate to different types of movement to actuate each mode of operation. For example, a single actuator may rotate for a first mode of operation, and slide in another mode. Or a single actuator may rotate in one direction for a first mechanical advantage, and rotate in another direction for a different mechanical advantage.

The present invention accordingly provides such a desirable method of using a medical device delivery mechanism, with an integrated and ergonomic handle replacing the functions of the separate proximal hubs of the prior inner and outer catheter shaft members, providing desired dual modes of operation as well as the desired locking system.

These and other various objects, and advantages and features of the invention will become apparent from the following description and claims, when considered in conjunction with the appended drawings.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a medical device delivery system is depicted, with one of the preferred embodiments of the present invention being shown at 10. The illustrated stent delivery catheter system 10 of course depicts only one of many different medical device delivery systems designs that are within the scope of the present invention. The present invention may be designed to deliver and deploy any suitable medical device. However, for clarity and convenience, the present detailed description will only describe such an example of a delivery system for stents.

Among the possible medical device delivery systems that may be used with the present invention is any appropriate system in which an outer sheath is provided, surrounding an inner shaft. A medical device may be carried within the outer sheath during delivery to a desired site for treatment, where the outer sheath may be retracted, while the inner shaft and medical device are held in place.

The novel concept of the present invention may also be used for medical device delivery systems in which the motion of the operator to deploy the medical device is selected from any suitable possibility, including axial motion in the proximal direction or distal direction, or a rotational motion, a trigger actuator, a gear mechanism, or any other type of actuator that may be preferred, depending upon a particular application. Indeed, the present unique concept may be used for medical device delivery systems in which the medical device is deployed in any suitable manner, including retracting an outer sheath in a proximal or distal direction, or uncovering a medical device in various ways, including withdrawing portions of outer sheath members in proximal and distal directions, simultaneously or sequentially.

The present invention may preferably have several advantages individually, or any combination of such advantages, including for example: (i) single-handed operation of the medical device delivery system; (ii) a mechanism providing leverage or mechanical advantage, to adjust or reduce the forces needed to operate the system; (iii) improved accuracy in positioning the medical device during deployment; and (iv) multiple operational modes of operation, including for example a first mode of fine and precise control of the deployment process, and a second mode of rapid and easy deployment.

Moreover, additional advantages may include: (i) an integrated and ergonomic handle for easily and effectively operating the stent delivery system of the present invention; (ii) a locking mechanism capable of resisting inadvertent or accidental movement or retraction of the stent delivery system components during packaging, sterilization, shipping, storage, handling and preparation; and (iii) a capability of holding the delivery system components in a fixed relative position during an intermediate point in deploying a medical device.

The particular embodiment of the present invention selected for illustration in the drawings includes a handle 10, shown in detail in FIGS. 1-10. An upper and lower main body housing 12 and 14 are arranged in a top-and-bottom configuration, as shown for example in FIGS. 1 and 3. Other components include inner and outer shaft members 16 and 18 respectively, an anchoring member 20, a proximal hub 22 with an actuator or knob 24 and a corresponding flush lumen tube 26, as well as a threaded base member 30 and a rotating finger ring 32.

In addition, the handle of the present invention preferably has a locking mechanism 28 for releasably locking the outer shaft member 18 in an initial position relative to the handle 10 and the inner shaft member 16, by resisting movement of the rotating finger ring 32 relative to the upper and lower body housings 12 and 14, and thus preventing motion of the threaded base 30 and proximal hub 22.

The lower main body housing 14 preferably has several gripping knurls 34 for providing a physician with a good gripping surface, while the upper main body housing 12 has a longitudinal slot 36 defining a channel for sliding the movable actuator 24 and thus limiting the extent of possible travel for the actuator 24 and proximal hub assembly 22. Together, the upper and lower body housings 12 and 14 define openings 38 through which a physician can operate the rotating finger ring 32, a proximal anchoring aperture 40 adapted to capture a portion of the anchoring member 20, a distal shaft aperture 42 through which the inner and outer shaft members 16 and 18 extend, and several internal openings for receiving fasteners 44 to hold the main body housings 12 and 14 together. They also define a circular annular bearing shelf or shoulder 46.

In the preferred initial configuration, proximal hub 22 is affixed to threaded base 30, which rotatably carries rotating finger ring 32. A distal surface of rotating finger ring 32 touches and bears on shoulder 46 of main body housing 12. Rotation of the rotating finger ring 32 causes it to press on shoulder 46 and pull on threaded base 30, resulting in very precise and sensitive withdrawing movement of outer shaft member 18 in a proximal direction. Then, when more rapid proximal withdrawal of the outer shaft member 18 is desired, the physician may grasp the actuator 24 and swiftly draw the hub 22 directly back in the proximal direction.

In the particular assembly shown in the drawings, main body housings 12 and 14 are held together by fasteners 44. Anchor aperture 40 fixedly receives anchor 20, which is affixed to the proximal end of inner shaft member 16. A proximal end of outer shaft member 18 is affixed to proximal hub 22, with a flexible strain relief 48 protecting the joint.

Figure 11:
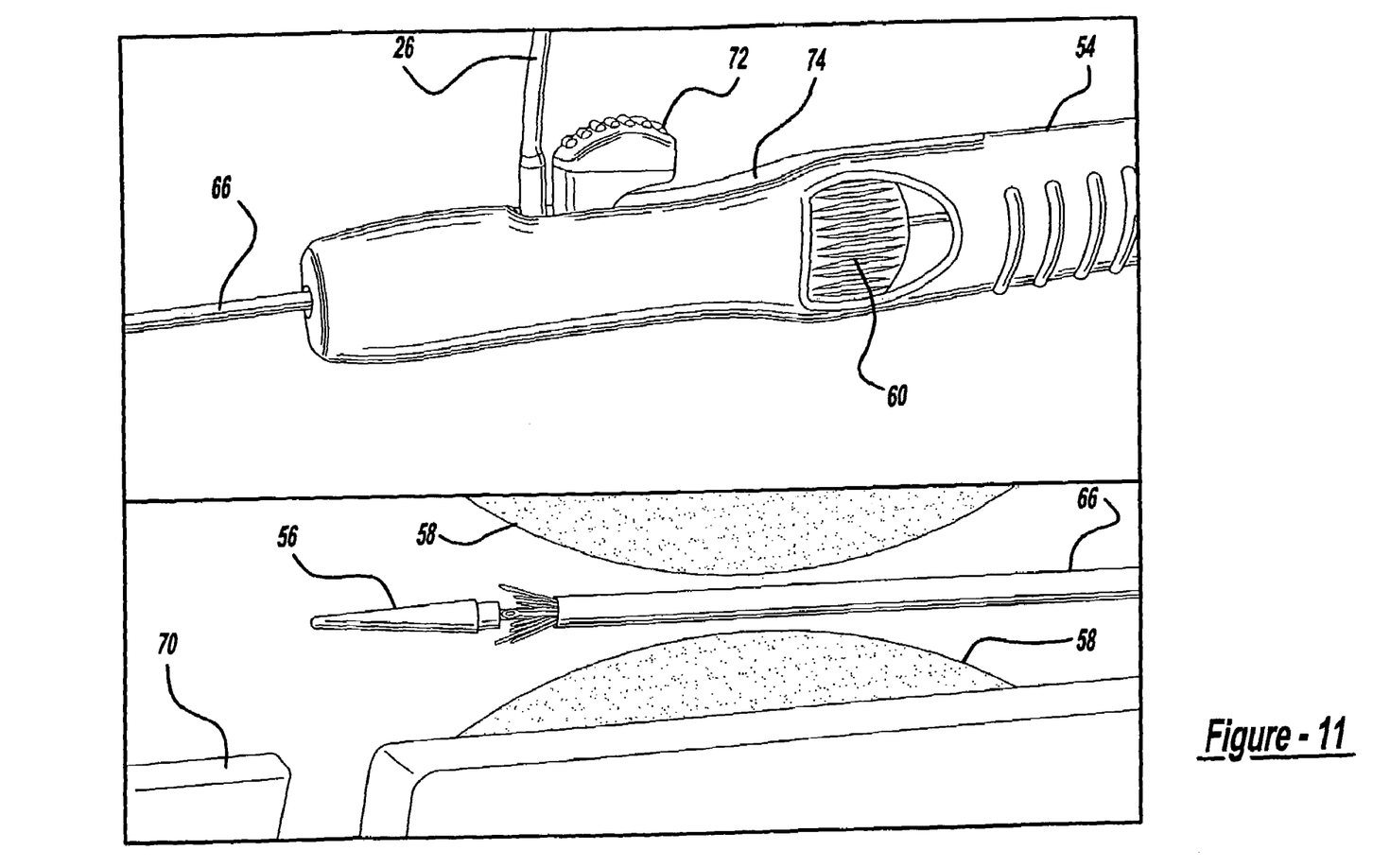
FIGS. 11-14 are perspective views of proximal and distal ends of a medical device delivery system arranged according to the principles of the present invention, in various operating configurations.

An example description of one method of operating the medical device delivery system of the present invention is graphically depicted in FIGS. 11-14, which include illustrations of a handle 54 having a different appearance than handle 10 shown in FIGS. 1-10. In operation, the distal end 56 of the medical device delivery system is preferably directed into a patient via a body passageway. The medical device delivery system may follow along a guidewire (not shown), and/or travel through a previously placed guiding catheter (not shown), until the distal end 56 is at a desired location for treatment. As shown in FIG. 11, the distal tip 56 has preferably crossed the site of a lesion or stenosis 58.

Figure 1:
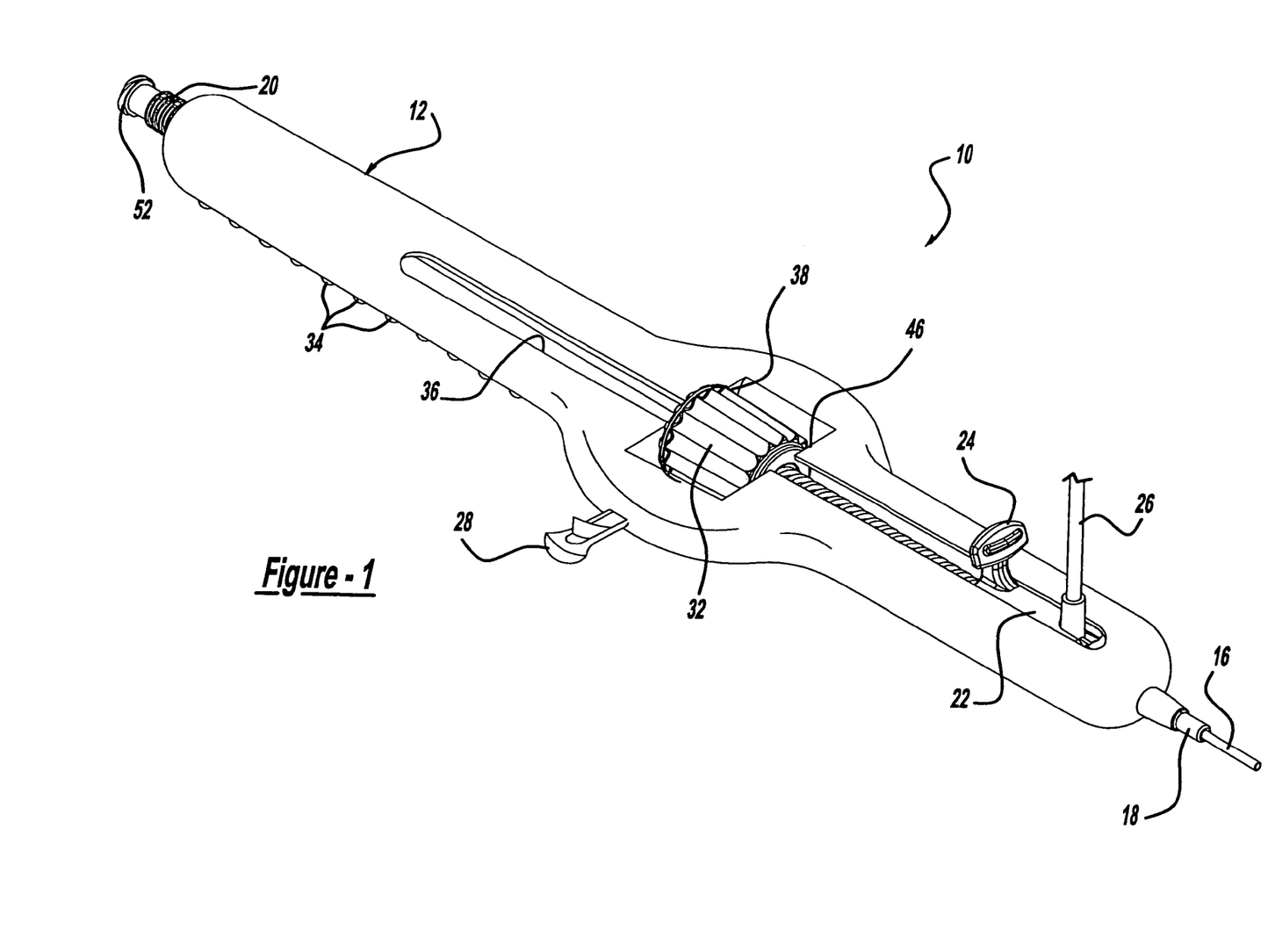
FIG. 1 is an external perspective view of a medical device delivery system handle, arranged according to the principles of the present invention.
Figure 2:
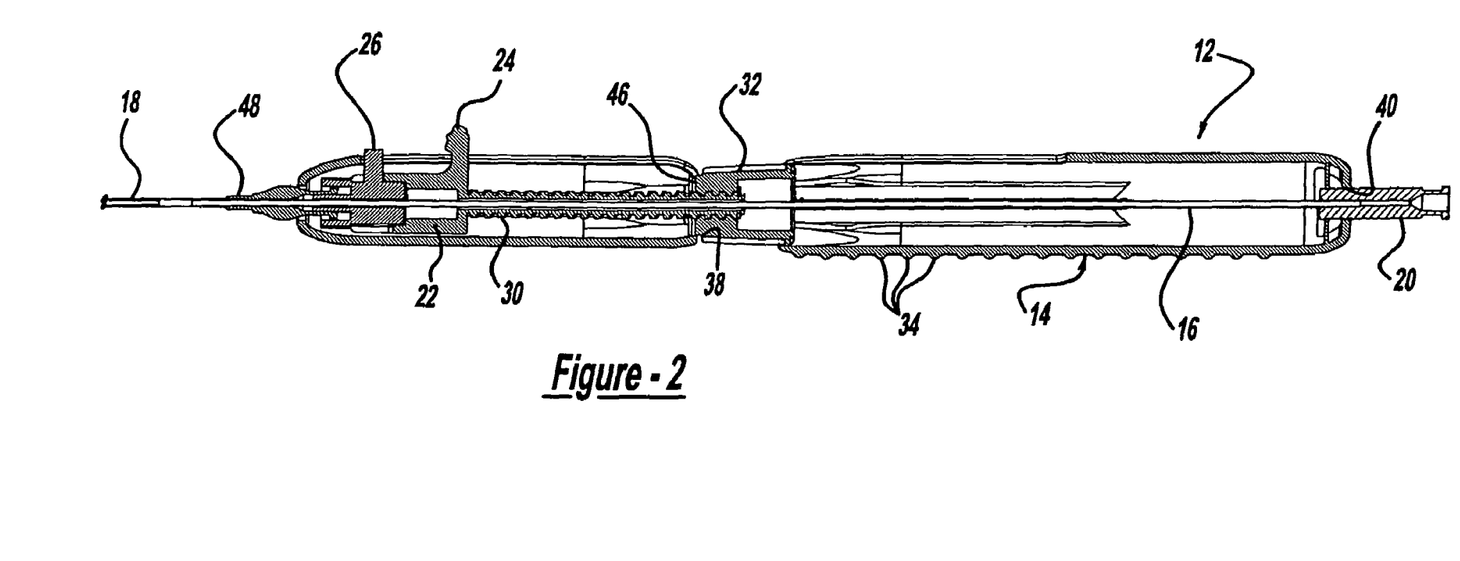
FIG. 2 is a partial longitudinal cross-sectional view of a medical device delivery system arranged according to the present invention in an initial configuration.
Figure 3:
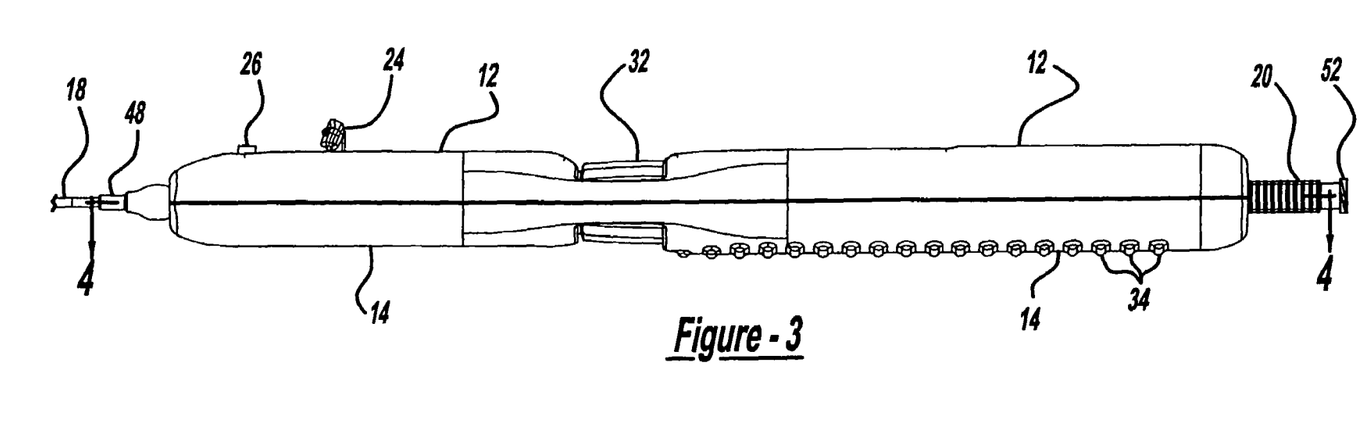
FIG. 3 is a partial side elevation view of the medical device delivery system of FIG. 2.
Figure 4:
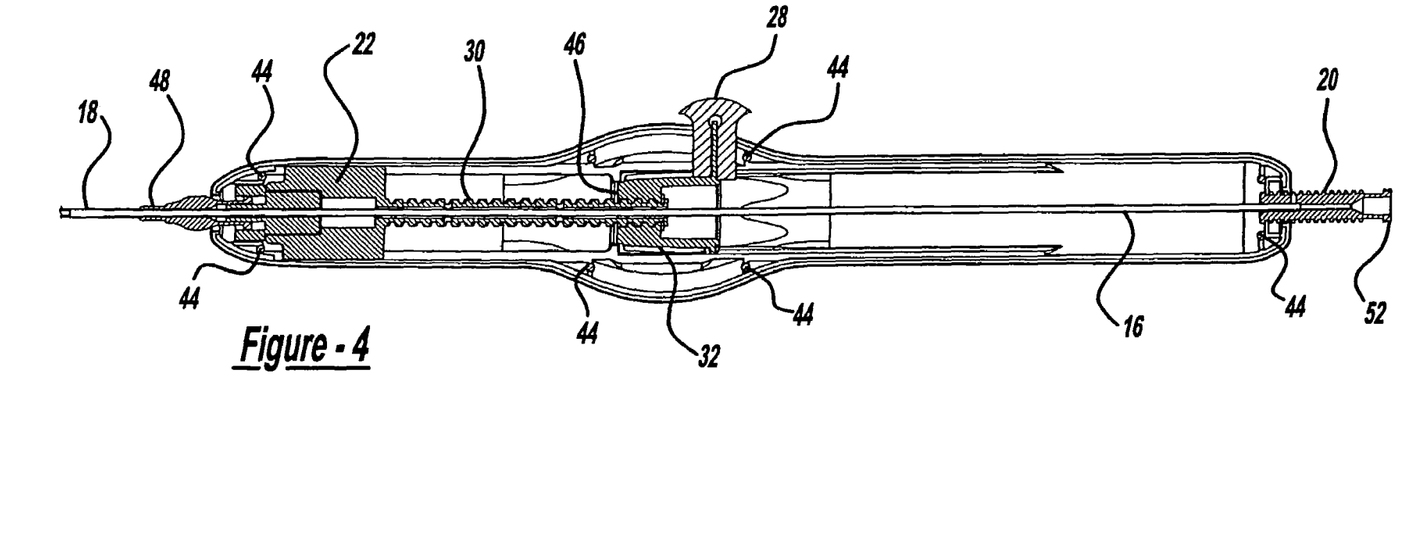
FIG. 4 is a partial top plan cross-sectional view of the medical device delivery system of FIG. 2.
Figure 5:
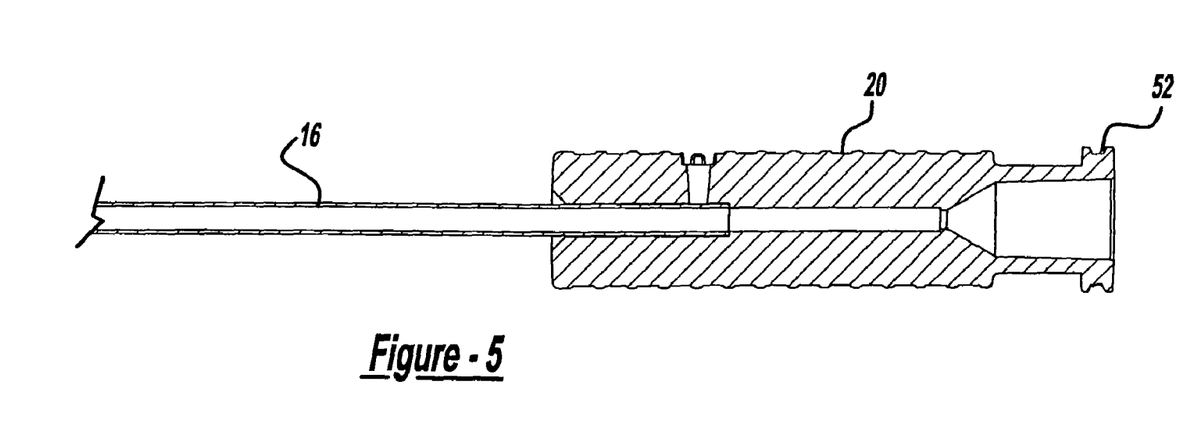
FIG. 5 is a partial longitudinal cross-sectional view of certain components of a medical device delivery system according to the present invention.
Figure 6:
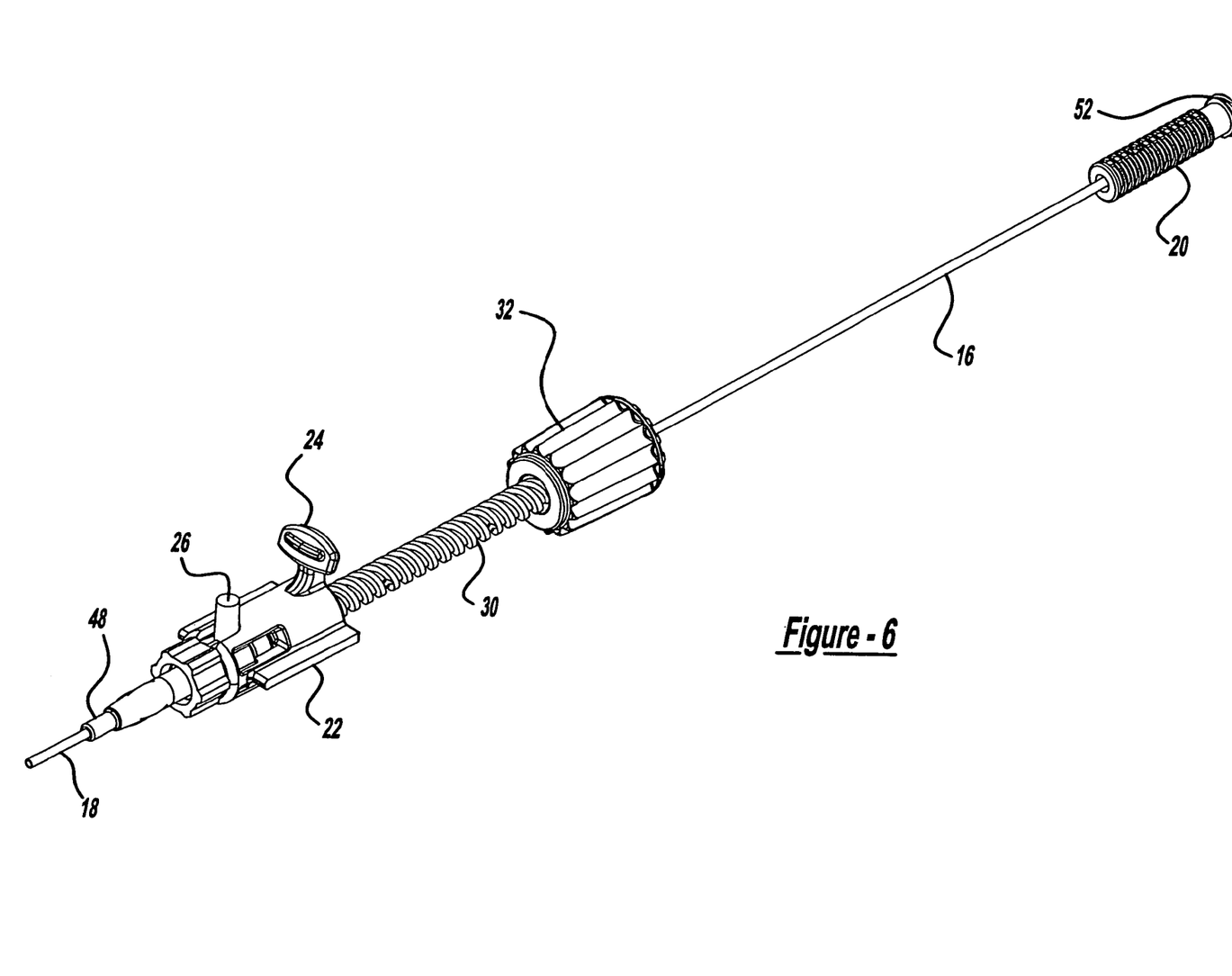
FIG. 6 is a perspective view of certain components of a medical device delivery system according to the present invention.
Figure 7:
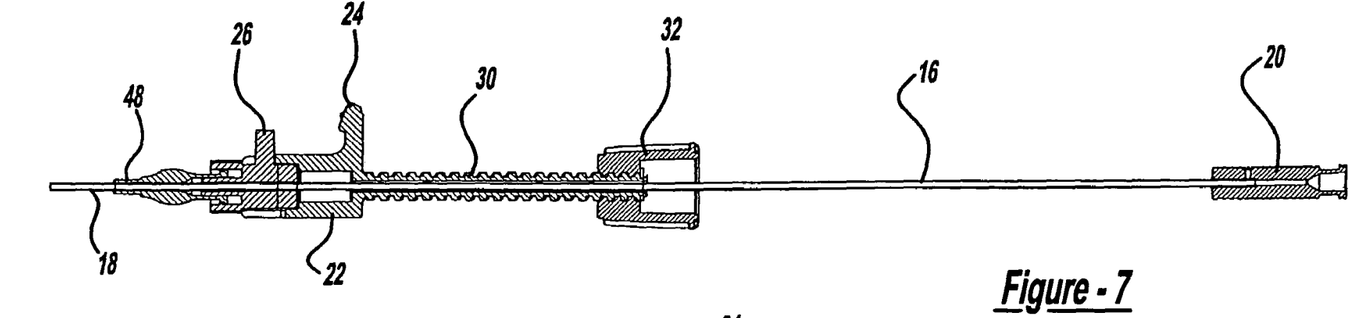
FIGS. 7-10 are partial longitudinal cross-sectional views of certain components of a medical device delivery system according to the present invention.
Figure 8:
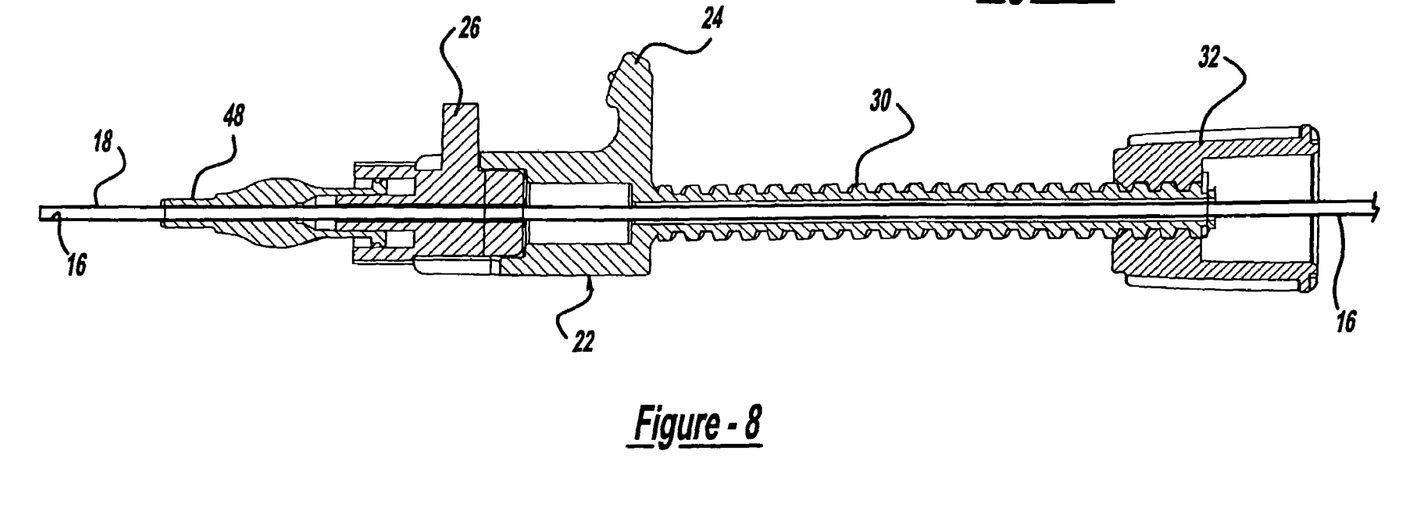
Figure 9:
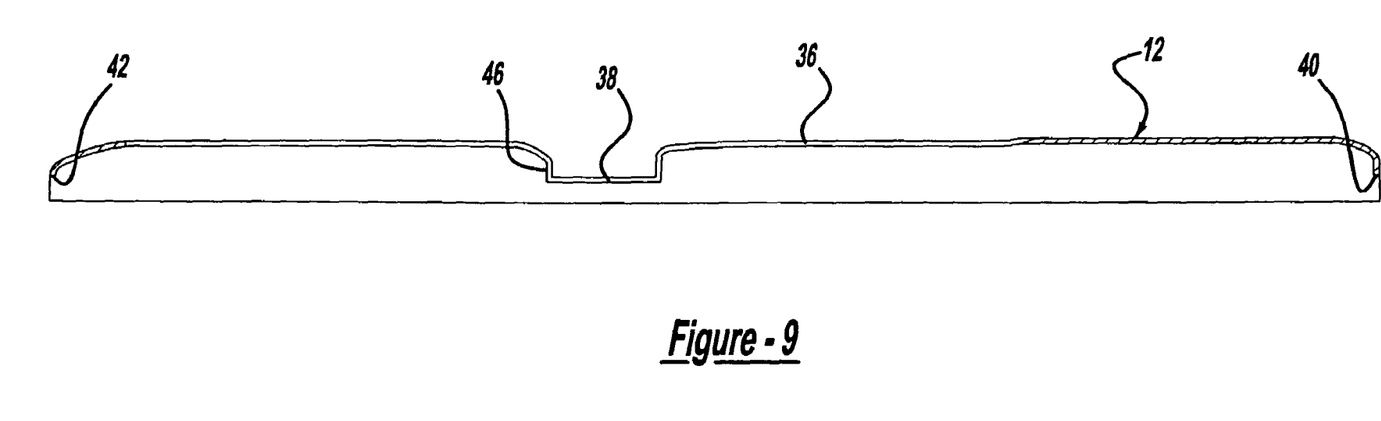

When the device is properly in an initial position, the physician releases or breaks off the lock of the present invention. A single embodiment of the lock is illustrated in FIGS. 1 and 4, and of course the present invention encompasses a multitude of various lock configurations, including pins, clamps, breakable members, spring-loaded locks, splines, or keys. The lock may be releasable only once, or may be capable of repeatedly being engaged and released. For example, the lock shown in FIGS. 1-10 may be initially released by squeezing the components, and then used to re-lock the system in another position or configuration, such as for example that shown in FIG. 13.

Such a locking mechanism preferably resists inadvertent or accidental movement or retraction of the stent delivery system components during packaging, sterilization, shipping, storage, handling and preparation.

After the lock is released, the preferred operation of the present invention may be accomplished by first rotating the finger ring 60 to cause it to advance on threaded base 62 and press against shoulder 64, such that the entire assembly of threaded base 62, proximal hub and outer shaft member 66 withdraw proximally with respect to handle 54, and thus with respect to inner shaft member 68. This first method of withdrawing the outer sheath 66 allows precise and sensitive adjustment.

Figure 12:
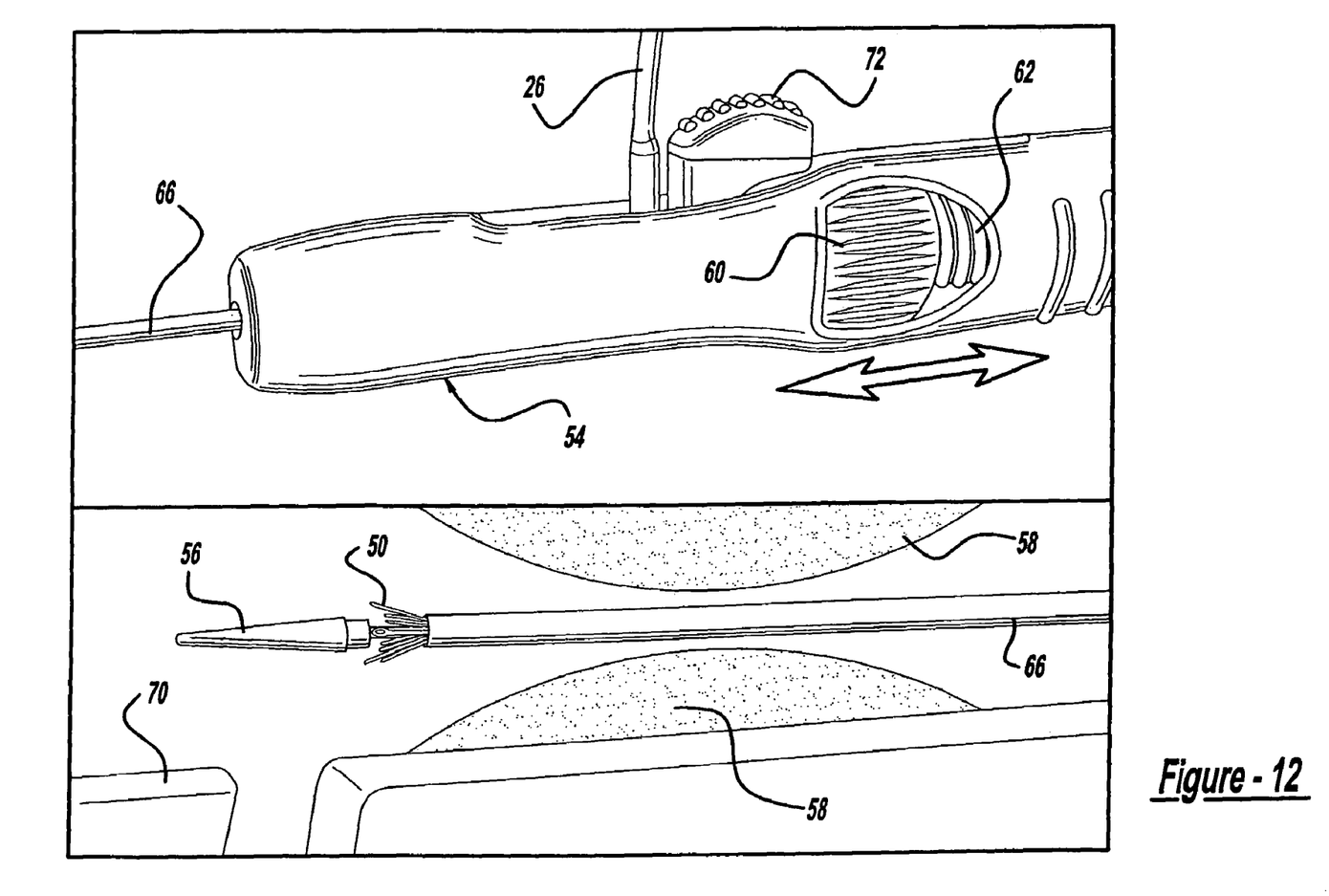

As shown in FIGS. 11 and 12, the physician may rotate the finger ring 60 slightly, to pull the outer sheath 66 back slightly. This small movement exposes a small portion of the medical device, in this case a stent 50, as shown in FIG. 12. In this configuration, the handle of the present invention will hold the outer sheath 66 in position relative to the inner body 68, resisting further inadvertent expansion of the stent 50. The physician then has the time and flexibility of procedure to selectively optimize and make any final adjustments to the position of the medical device and delivery system within the desired site, as illustrated by the arrow in FIG. 12. This precise adjustment of the position of the stent 50, before any portion of the stent 50 touches the body passage or vessel 70 in a manner that might inhibit further positional adjustment, is preferable.

Figure 13:
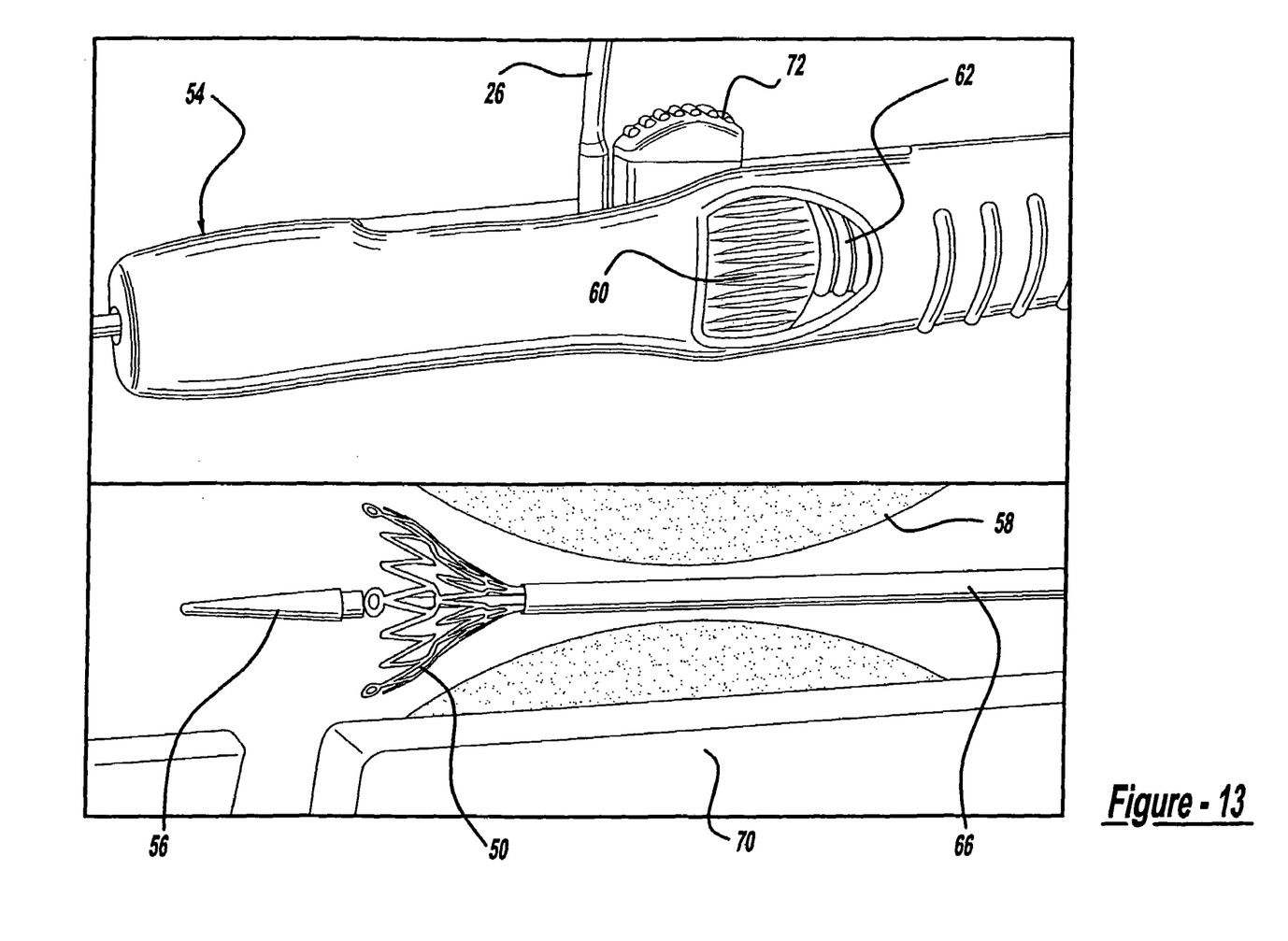

When the physician is satisfied with the positioning, as it appears on a fluoroscopic x-ray video screen, the physician may continue to rotate the finger ring 60 to further withdraw the outer sheath 66, as shown in FIG. 13.

Figure 14:
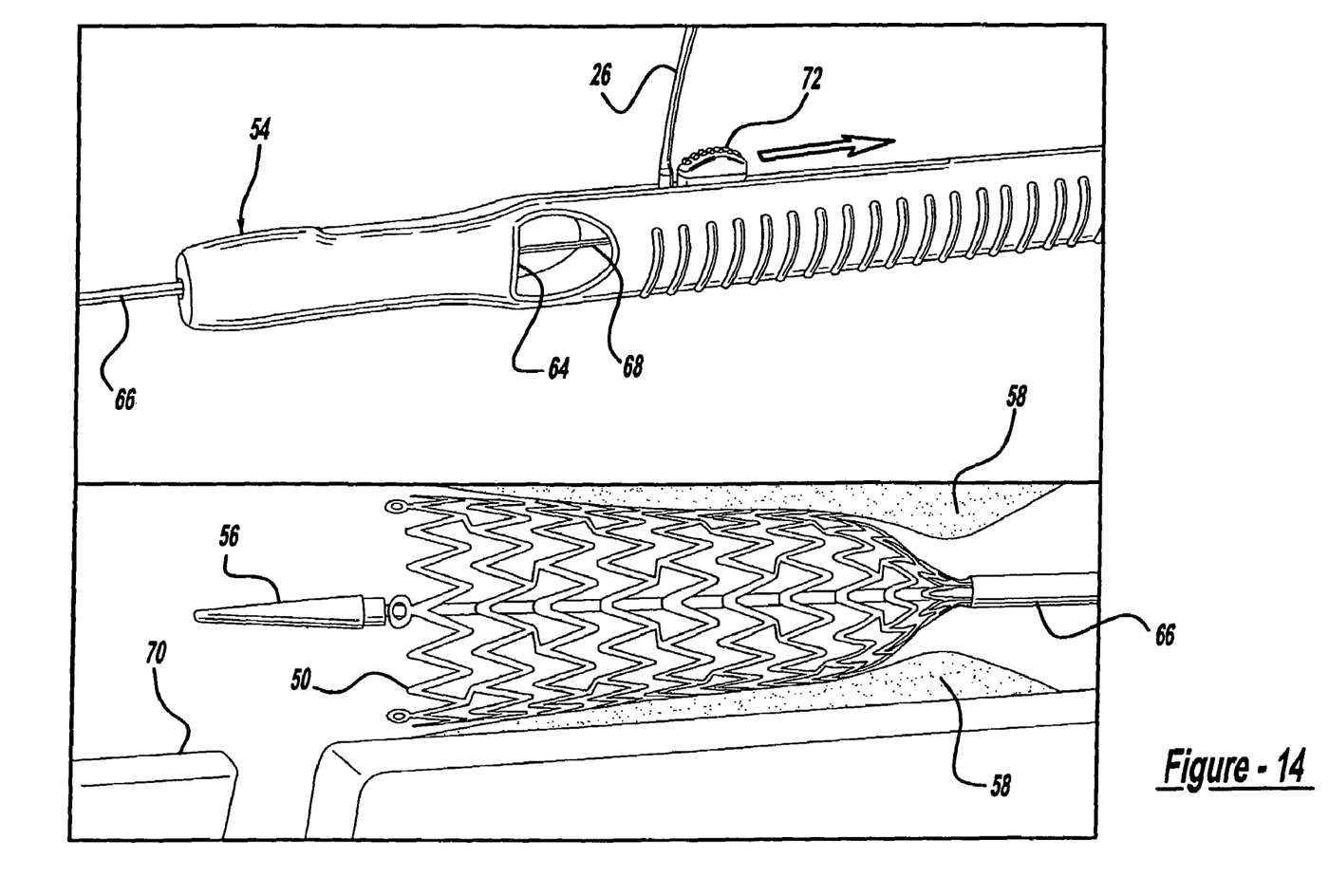

Upon initial contact of the stent 50 with the vessel wall, or when the stent is expanded sufficiently to independently hold its position, or at any desired point, the physician may simply grasp knob 72 and pull or push it along slot 74, as depicted by the arrow in FIG. 14. This second method of withdrawing the outer sheath 66 allows relatively large-scale and rapid movement, at whatever speed the physician wishes, to quickly deploy the medical device.

Various materials may be selected for the components of the present invention, including any material having the desirable performance characteristics. In the particular embodiment shown in the drawings, the inner and outer shaft members 16 and 18, strain relief 48, and distal tip 56 may be made of any biocompatible and suitably flexible yet sufficiently strong material, including polymers of various types. Possible selections for such materials include nylons or polyamides, polyimides, polyethylenes, polyurethanes, polyethers, polyesters, etc. In the alternative, some portion or all of the inner and/or outer shaft member 16, 18 may be formed of a flexible metal, including for example stainless steel or nitinol hypotube. The stent 50 is preferably made of any biocompatible material that is strong and flexible with high hoop strength, including for example stainless steel, platinum, tungsten, etc. The components of the handle of the present invention are preferably made of a material that is strong and rigid, including for example inflexible polycarbonates, or even some metal components.

Of course, many different variations are included within the scope of the present invention. Some of these variations or alternative embodiments include any possible arrangement of sizes, materials, and designs within the bounds of the following claims.

In addition, the inner shaft member 16 assembly, including anchor 20, inner shaft member 16 and distal tip 56, may preferably be provided with a through lumen adapted to receive a guidewire.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A method for therapeutically treating a patient, comprising the steps of:
   (a) providing a medical device delivery system having an inner shaft and a tubular outer sheath, each with proximal and distal ends; a handle near the proximal ends of the inner shaft and outer sheath; a medical device for delivery by the delivery system and for performing a therapeutic procedure at a desired site for treatment; a delivery mechanism for selectively and progressively pulling the outer sheath in the proximal direction to release the medical device; and a locking member that holds the delivery mechanism in an initial configuration, the locking member tending to releasably resist inadvertent release of the medical device by the delivery mechanism;
   wherein the medical device is positioned within the outer sheath in an initial configuration; wherein the handle has a first and second independently movable actuator coupled to the delivery mechanism;
   (b) inserting the medical device delivery system along a body passage until the medical device is positioned at or near the desired site for treatment;
   (c) unlocking the locking member;
   (d) moving the first actuator a first selected amount; such movement of the first actuator causing the outer sheath to move an amount in the proximal direction at a first proportional rate in a precise manner, and causing the outer sheath to partially release the medical device;
   (e) moving the second actuator, causing the outer sheath to move in the proximal direction at a second greater proportional rate in a rapid manner, to fully release the medical device; and
   (f) withdrawing and removing the medical device delivery system from the body passage, and allowing the medical device to remain at the desired site for treatment.

2. The method as set forth in claim 1, further comprising, between steps (d) and (e), the additional steps of; evaluating in greater detail the position of the medical device compared to the position of the desired site to be treated; and adjusting the position of the medical device delivery system based on the evaluation.

3. The method of claim 1, wherein the medical device is a self-expanding stent.

4. The method of claim 1, wherein the locking member is adapted to unlock only once.

5. The method of claim 1, wherein the locking member breaks during said unlocking step (c).

6. A method for therapeutically treating a patient, comprising the steps of:
   (a) providing a medical device delivery system having an inner shaft and a tubular outer sheath, each with proximal and distal ends; a handle near the proximal ends of the inner shaft and outer sheath; a medical device for delivery by the delivery system and for performing a therapeutic procedure at a desired site for treatment; a delivery mechanism for selectively and progressively pulling the outer sheath in the proximal direction to release the medical device; and a locking member that holds the delivery mechanism in an initial configuration, the locking member tending to releasably resist inadvertent release of the medical device by the delivery mechanism;
   wherein the medical device is positioned within the outer sheath in an initial configuration; the handle has a first and second independently movable actuator coupled to the delivery mechanism; the first actuator is rotatable knob; and the second actuator is a longitudinal slider;
   (b) inserting the medical device delivery system along a body passage until the medical device is positioned at or near the desired site for treatment;
   (c) unlocking the locking member,
   (d) rotating the first actuator a selected amount; such rotation of the first actuator causing the outer sheet to move an amount in the proximal direction at a first proportional rate in a precise manner, and causing the outer sheath to partially release the medical device;
   (e) sliding the second actuator longitudinally, causing the outer sheath to move in the proximal direction at a second greater proportional rate in a rapid manner, to fully release the medical device; and
   (f) withdrawing and removing the medical device delivery system from the body passage, and allowing the medical device to remain at the desired site for treatment.

7. The method as set forth in claim 6, further comprising, between steps (d) and (e), the additional steps of: evaluating in greater detail the position of the medical device compared to the position of the desired site to be treated; and adjusting the position of the medical device delivery system based on the evaluation.

8. The method as set forth in claim 6, wherein the second proportional rate is 1:1.

* * * * *